US011517273B2

(12) United States Patent
Lee et al.

(10) Patent No.: US 11,517,273 B2
(45) Date of Patent: Dec. 6, 2022

(54) DUAL ENERGY X-RAY IMAGING APPARATUS

(71) Applicant: RE-MEDI CO., LTD., Chuncheon-Si (KR)

(72) Inventors: Re Na Lee, Seoul (KR); Suk Young Shin, Seoul (KR)

(73) Assignee: RE-MEDI CO., LTD., Chuncheon-Si (KR)

( * ) Notice: Subject to any disclaimer, the term of this patent is extended or adjusted under 35 U.S.C. 154(b) by 0 days.

(21) Appl. No.: 17/137,682

(22) Filed: Dec. 30, 2020

(65) Prior Publication Data
US 2021/0145378 A1    May 20, 2021

Related U.S. Application Data

(63) Continuation of application No. PCT/KR2019/008048, filed on Jul. 2, 2019.

(30) Foreign Application Priority Data

Jul. 24, 2018   (KR) .................. 10-2018-0085903

(51) Int. Cl.
*A61B 6/00*     (2006.01)
*A61B 6/03*     (2006.01)

(52) U.S. Cl.
CPC .......... *A61B 6/4035* (2013.01); *A61B 6/032* (2013.01); *A61B 6/4208* (2013.01); *A61B 6/482* (2013.01); *A61B 6/5211* (2013.01)

(58) Field of Classification Search
CPC ..... A61B 6/4035; A61B 6/032; A61B 6/4208; A61B 6/482; A61B 6/5211; A61B 6/4042; A61B 6/42; A61B 6/5205
See application file for complete search history.

(56) References Cited

U.S. PATENT DOCUMENTS

2007/0019784 A1*   1/2007 Ting .................. G21K 1/10
                                                    378/21

FOREIGN PATENT DOCUMENTS

| KR | 10-1081411 B1     | 11/2011 |
|----|-------------------|---------|
| KR | 10-2013-0010952 A | 1/2013  |
| KR | 10-2015-0041239 A | 4/2015  |
| KR | 10-2016-0079961 A | 7/2016  |

* cited by examiner

*Primary Examiner* — Courtney D Thomas
(74) *Attorney, Agent, or Firm* — United One Law Group LLC; Kongsik Kim; Jhongwoo Peck

(57) ABSTRACT

Disclosed herein is a dual energy X-ray imaging apparatus. The dual energy X-ray imaging apparatus includes: an X-ray generator configured to generate a predetermined dose of X-rays; an X-ray detector configured to detect the X-rays received from the X-ray generator; an X-ray filter located between the X-ray generator and the X-ray detector, and configured to filter out part of the generated X-rays so that X-rays of two dose types reach the X-ray detector; and a medical image processing unit configured to generate medical images corresponding to the two dose types recognized by the X-ray detector.

4 Claims, 13 Drawing Sheets

FIG. 8

| | | 810 | | | | | | | 820 |
|---|---|---|---|---|---|---|---|---|---|
| LOWER | LOWER | HIGHER | HIGHER | | | | | | |
| LOWER | LOWER | HIGHER | HIGHER | | | | | | |
| HIGHER | HIGHER | LOWER | LOWER | | | | | | |
| HIGHER | HIGHER | LOWER | LOWER | | | | | | |
| | | | | | | | | | |
| | | | | | | | | | |
| | | | | | | | | | |
| | | | | | | | | | |

[RESULTS OF DOSES ACQUIRED ACCORDING TO THE THICKNESS OF AN X-RAY FILTER]

FIG. 12

| Unit: % | 0.1mm | 0.5mm | 1.0mm |
|---|---|---|---|
| Pb | 22.90 | 2.21 | 0.33 |
| Cu | 53.20 | 17.40 | 7.44 |
| Nb | 32.88 | 5.19 | 1.22 |
| Au | 14.93 | 0.76 | 0.08 |
| Sn | 36.00 | 3.35 | 0.48 |

FIG. 13

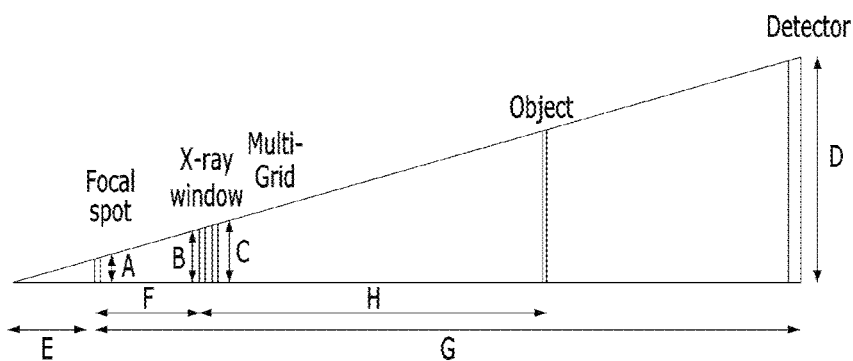

[THE CALCULATION OF THE TRIGONOMETRIC RATIO FOR DETERMINING THE SIZE OF THE ATTENUATING AND TRANSMISSION PORTIONS OF THE X-RAY FILTER(13-A)]

|   | FORMULA | RESULT |
|---|---|---|
| A | Focal spot의 ½ | 0.25 mm |
| B | X-ray Window ½ | 50 mm |
| C | E:A−(E+G) :D | 1.066 mm |
| D | CT 센서의 ½ | 119.38 mm |
| E | E:A−(E+G): D | 1.88 mm |
| F | E+F : B−E+G : D | 375.85 mm |
| G | FDD(Focla spot-Detetor-Distance) | 900 mm |
| H | FOD(Focla spot-Object-Distance) | 643 mm |

[PARAMETERS FOR DETERMINING THE SIZES OF THE ATTENUATING AND TRANSMISSION PORTIONS OF THE X-RAY FILTER(13-B)]

DUAL ENERGY X-RAY IMAGING APPARATUS

CROSS-REFERENCE TO RELATED APPLICATION

This application is a Continuation of PCT/KR2019/008048 filed on Jul. 2, 2019, which claims priority to Korean Patent Application No. 10-2018-0085903 filed on Jul. 24, 2018, which applications are incorporated herein by reference in their entirety.

TECHNICAL FIELD

The present invention relates generally to a dual energy X-ray imaging apparatus, and more particularly to a dual energy X-ray imaging apparatus that is capable of generating a higher-dose, lower-energy image and a lower-dose, higher-energy image by radiating X-rays once and partially attenuating the X-rays using an X-ray filter.

BACKGROUND ART

An X-ray imaging apparatus is an apparatus for acquiring X-ray images of bones or organs by generating X-rays and projecting the generated X-rays onto a human or animal. The health status of the human or animal can be diagnosed through the acquired images. X-rays are projected in order to acquire X-ray images of bones or organs. There are people or animals that exhibit clear distinctions between bones and organs. However, in the case of patients with low bone density in some humans or animals, there may be cases where it is difficult to distinguish between bones and organs in X-ray images because the difference in density between soft tissues and hard tissues, such as bones, is small in the X-ray images. Accordingly, there is a demand for an X-ray imaging apparatus capable of acquiring X-ray images having high contrasts between hard and soft tissues by radiating X-rays only once.

Korean Patent Application Publication No. 10-2016-0079961 entitled "X-ray Fluoroscopy Apparatus using Dual Energy Level X-ray Source" discloses a technology related to an X-ray imaging device that is capable of acquiring X-ray images having high contrasts between hard and soft tissues by radiating higher-energy level X-rays and lower-energy level X-rays.

The above prior art has a problem in that the human body is exposed to a relatively high dose of radiation by radiating both higher-energy level X-rays and lower-energy level X-rays, thereby causing harm to the human body. Therefore, there is a demand for an X-ray imaging apparatus that is capable of acquiring X-ray images having high contrasts between hard and soft tissues by radiating X-rays onto the human body only once.

SUMMARY OF THE DISCLOSURE

An object of the present invention is to provide a dual-energy X-ray imaging apparatus so that the human body may be exposed to less radiation and also X-ray images of two different dose types may be acquired by radiating X-rays only once.

An object of the present invention is to allow two types of X-rays, i.e., a lower dose of high-energy X-rays and a higher dose of low-energy X-rays, to be generated using a single filter by attenuating or not attenuating a predetermined dose of generated X-rays.

An object of the present invention is to allow X-ray images to be more easily estimated using X-rays filtered through attenuation and transmission portions by applying a filter having a specific grid pattern and thus arranging the attenuation and transmission portions regularly.

An object of the present invention is to allow the boundary surfaces between attenuation and transmission portions to be inclined toward an X-ray generator, so that X-rays are not transmitted through both attenuation and transmission portions but are transmitted through only one of the attenuation and transmission portions, thereby enabling generated X-rays to be more accurately recognized.

An object of the present invention is to allow the thickness of attenuation portions to gradually decrease in outward directions from the point onto which an X-ray is vertically radiated by an X-ray detector, so that the dose of attenuated X-rays for X-rays radiated vertically and the dose of attenuated X-rays for X-rays radiated at an inclined angle may be made the same.

An object of the present invention is to allow the size of attenuation and transmission portions to be an integer multiple of the minimum measurement unit area of an X-ray detector, so that the minimum measurement unit of the X-ray detector recognizes only an X-ray transmitted through one of the attenuation and transmission portions, thereby clearly distinguishing between a lower dose of X-rays and a higher dose of X-rays.

An object of the present invention is to generate a higher-dose image by estimating empty portions corresponding to a lower dose of X-rays based on recognized information about portions corresponding to a higher dose of X-rays, so that two types of X-ray images may be generated by filtering out part of X-rays, radiated once, using a single X-ray filter.

According to an aspect of the present invention, there is provided a dual energy X-ray imaging apparatus including: an X-ray generator configured to generate a predetermined dose of X-rays; an X-ray detector configured to detect the X-rays received from the X-ray generator; an X-ray filter located between the X-ray generator and the X-ray detector, and configured to filter out part of the generated X-rays so that X-rays of two dose types reach the X-ray detector; and a medical image processing unit configured to generate medical images respectively corresponding to the two dose types recognized by the X-ray detector.

The X-ray filter may include: attenuation portions made of at least one of lead, copper, niobium, stannum, and gold, and configured to attenuate the predetermined dose of the generated X-rays; and transmission portions configured to transmit a higher dose of X-rays than the attenuation portions therethrough.

The attenuation portions and the transmission portions may be arranged to form a grid pattern.

The boundary surfaces between the attenuation portions and the transmission portions may be inclined toward the X-ray generator.

The thickness of the attenuation portions may gradually decrease in outward directions from the point at which an X-ray is vertically radiated onto the X-ray detector.

The size of the attenuation and transmission portions may be determined such that an area formed on a surface of the X-ray detector by X-rays transmitted through one of the attenuation portions or X-rays transmitted through one of the transmission portions is an integer multiple of the minimum measurement unit area of the X-ray detector.

The medical image processing unit may be further configured to generate a temporary higher-dose image in which portions corresponding to a lower dose type are empty based on recognized information about portions corresponding to a higher one of the two dose types recognized by the X-ray detector and to estimate the empty portions based on the information of the temporary higher-dose image, thereby generating a final higher-dose image.

BRIEF DESCRIPTION OF THE DRAWINGS

The above and other objects, features and advantages of the present invention will be more clearly understood from the following detailed description taken in conjunction with the accompanying drawings, in which:

FIG. 8 is a diagram illustrating an example in which the size of attenuation and transmission portions is an integer multiple of the unit area of a sensor for detecting X-rays according to an embodiment of the present invention;

FIG. 12 is a diagram illustrating the ratio of an output photon quantity to an incident photon quantity per the material and thickness of an X-ray filter according to an embodiment of the present invention; and FIG. 13 is a diagram illustrating an example of the calculation of the trigonometric ratio for determining the size of the attenuating and transmission portions of the X-ray filter and parameters for determining the sizes of the attenuating and transmission portions of the X-ray filter according to an embodiment of the present invention.

DETAILED DESCRIPTION OF THE DISCLOSURE

Figure 1:
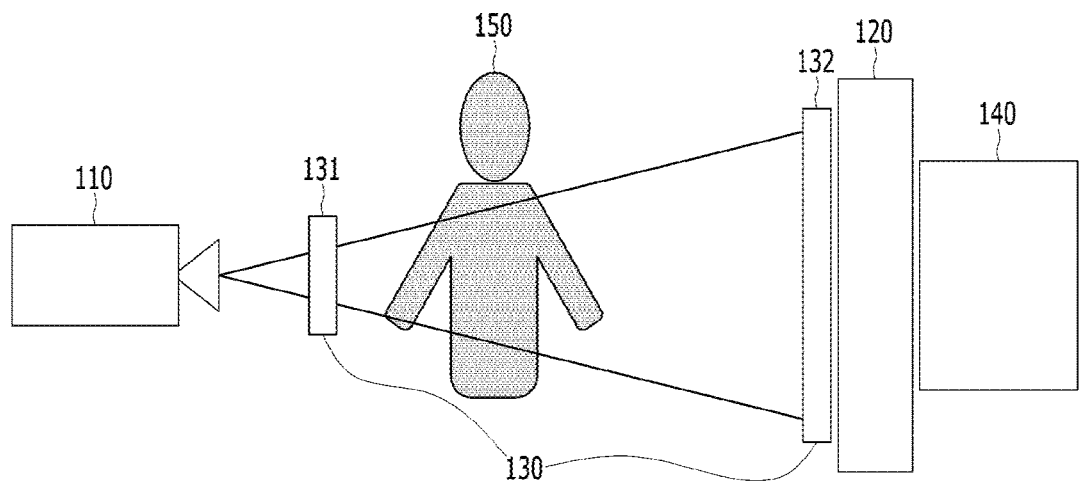
FIG. 1 is a diagram showing an example of the configuration of a dual energy X-ray imaging apparatus according to an embodiment of the present invention.

FIG. 1 is a diagram showing an example of the configuration of a dual energy X-ray imaging apparatus according to an embodiment of the present invention.

The present invention is directed to a dual energy X-ray imaging apparatus applicable to both a computed tomography (CT) apparatus and an X-ray apparatus. The dual energy X-ray imaging apparatus includes an X-ray generator 110, an X-ray detector 120, an X-ray filter 130 including attenuation portions 210, and transmission portions 220, and a medical image processing unit 140.

The X-ray generator 110 generates a predetermined dose of X-rays.

The X-ray generator 110 may be an X-ray source or X-ray tube that generates X-rays, and may be a device formed by combining devices required for the generation of X-rays, such as a high-voltage transformer, a rectifier, a controller, and an X-ray tube.

The X-ray detector 120 detects an X-ray received from the X-ray generator 110.

The X-ray detector 120 is intended to detect X-rays, and may perform amplification using fluorescence based on X-rays other than a film and dry plate for X-rays and a fluorescent plate. When the X-ray detector 120 is placed on an object to be X-rayed and X-rays are radiated using the X-ray generator 110, the X-ray detector 120 may detect the X-rays generated by the X-ray generator 110 and generate the X-ray information of the object to be X-rayed.

The X-ray filter 130 is located between the X-ray generator 110 and the X-ray detector 120 and filters out part of the generated X-rays, thereby allowing X-rays of two dose types to reach the X-ray detector 120.

The X-rays of two dose types, which reach the X-ray detector 120, may be a higher dose of lower-energy X-rays and a lower dose of higher-energy X-rays. The X-rays generated by the X-ray generator include both low energy and high energy. The X-rays transmitted through the X-ray filter 130 may be a lower dose of higher-energy X-rays because lower-energy X-rays are filtered out and only higher-energy X-rays are output. In contrast, the X-rays transmitted through unfiltered areas may be expressed as a higher dose of lower/higher-energy X-rays because both low- and higher-energy X-rays of a higher dose type can reach the X-ray detector 120. In order to clearly distinguish them from a lower dose of higher-energy X-rays, they may be expressed as a higher dose of lower-energy X-rays.

When the X-ray generator 110 radiates X-rays toward an object to be X-rayed, the X-ray detector 120 detects the X-rays radiated by the X-ray generator 110. The object is located between the X-ray generator 110 and the X-ray detector 120. The X-ray filter 130 may be located between the X-ray generator 110 and the X-ray detector 120. The X-ray filter 130 may be located closer to the X-ray generator 110 (in the case of 131) or may be located closer to the X-ray detector 120 (in the case of 132). In other words, when the X-ray filter 130 is located closer to the X-ray generator 110, the components of the X-ray imaging apparatus are disposed in the order of the X-ray generator 110, the X-ray filter 130, an object, and the X-ray detector 120. In contrast, when the X-ray filter 130 is located closer to the X-ray detector 120, the components of the X-ray imaging apparatus are disposed in the order of the X-ray generator 110, an object, the X-ray filter 130, and the X-ray detector 120.

The X-ray filter 130 outputs the X-rays, generated by the X-ray generator 110, as a lower dose of X-rays or a higher dose X-rays through filtering. Accordingly, the X-ray detector 120 may recognize X-rays as if the X-ray generator 110 radiates a lower dose of high-energy X-rays or a higher dose of X-rays. In other words, when the X-ray generator 110 radiates one type of X-rays toward an object, the X-ray filter 130 may output the X-rays, generated by the X-ray generator 110, as a higher dose of X-rays and a lower dose of X-rays through filtering. The X-ray detector 120 recognizes X-rays of two dose types (a higher dose of X-rays and a lower dose of X-rays) filtered by the X-ray filter 130. Accordingly, there may be achieved an effect identical to the effect achieved when the X-ray generator 110 radiates X-rays of two dose types.

The X-ray filter 130 includes attenuation portions 210 made of at least one of lead, copper, niobium, stannum, and gold and configured to attenuate the predetermined dose of the generated X-rays, and transmission portions 220 configured to transmit a higher dose of X-rays than the attenuation portions 210 therethrough.

Various types of constituent materials used for the material optimization of the X-ray filter 130 may include copper mainly applied to a filter for X-ray imaging, niobium applied to a filter for the acquisition of dental X-ray images, stannum applied to and used for a filter for dual energy CT equipment, and gold. In order to optimize the thickness of the X-ray filter 130, the thickness of each material of lead, copper, niobium, stannum, and gold may be equal to or higher than about 0.1 mm and lower than or equal to about 1.0 mm.

The attenuation portions 210 of the X-ray filter 130 may receive the X-rays generated by the X-ray generation unit and output a lower dose of X-rays. The transmission portions 220 of the X-ray filter 130 may receive the X-rays generated by the X-ray generation unit and transmit a higher dose of X-rays. Accordingly, the X-ray filter 130 may filter the X-rays generated by the X-ray generation unit and output X-rays of two dose types, i.e., a lower dose of higher-energy X-rays and a higher dose of lower-energy X-rays.

The attenuation portions 210 and the transmission portions 220 may be arranged to form a grid pattern.

The attenuation and transmission portions 210 and 220 of the X-ray filter 130 may be disposed in the grid pattern. When this X-ray filter 130 is exposed to the generated X-rays, a lower dose of X-rays are output through the attenuation portions 210, and a higher dose of X-rays are output through the transmission portions 220. The filtered X-rays may be received by the X-ray detector 120 and recognized based on the grid pattern of the X-rays.

The attenuation portions 210 and the transmission portions 220 may be arranged to form a stripe pattern in which the attenuation portions 210 and the transmission portions 220 are alternately arranged.

The attenuation and transmission portions 210 and 220 of the X-ray filter 130 may be disposed in the stripe pattern. When this X-ray filter 130 is exposed to the generated X-rays, a lower dose of X-rays are output through the attenuation portions 210, and a higher dose of X-rays are output through the transmission portions 220. The filtered X-rays may be received by the X-ray detector 120 and recognized based on the stripe pattern of the X-rays.

The boundary surfaces between the attenuation portions 210 and the transmission portions 220 are inclined toward the X-ray generator 110.

The X-ray generator 110 radiates X-rays toward the X-ray detector 120. When X-rays are radiated from the X-ray generator 110 toward the X-ray detector 120, the X-rays are radiated in a form spreading from the X-ray generator 110 to the X-ray detector 120. When viewed from the X-ray generator 110 and the X-ray detector 120, the X-rays are radiated at inclined angles rather than straight forward. Depending on the directions in which X-rays are radiated, the directions of the attenuation portions 210 and transmission portions 220 of the X-ray filter 130 are also inclined toward the X-ray generator 110. In the case where the boundary surfaces between the attenuation portions 210 and the transmission portions 220 are inclined toward the X-ray generator 110, when the X-ray generator 110 radiates X-rays toward the X-ray filter 130, the X-rays may be more accurately transmitted through the attenuation portions 210 and the transmission portions 220, and thus the X-rays may be more accurately filtered.

In the case where the boundary surfaces between the attenuation and transmission portions 210 and 220 of the X-ray filter 130 are not inclined toward the X-ray generator 110 but are vertical (in the case of 410), when the X-ray generator 110 radiates X-rays toward the X-ray detector 120 at inclined angles, there may occur a case 420 where an X-ray is transmitted through both the attenuation portion 210 and the transmission portion 220. When an X-ray is radiated while being transmitted through both the attenuation portion 210 and the transmission portion 220, there occurs the effect in which the X-ray is transmitted and is also attenuated, and thus a problem arises in that the X-ray may not be accurately filtered. In contrast, in the case where the boundary surfaces between the attenuation portions 210 and the transmission portions 220 are inclined toward the X-ray generator 110, a case where an X-ray is transmitted through both the attenuation portion 210 and the transmission portion 220 does not occur, and thus an advantage arises in that X-rays may be accurately filtered.

The thickness of the attenuation portions 210 gradually decreases in outward directions from the point at which an X-ray is vertically radiated onto the X-ray detector 120.

When the X-ray generator 110 radiates X-rays, the X-rays are radiated from the X-ray generator 110 in the direction of the X-ray detector 120. In this case, the X-rays radiated by the X-ray generator 110 are radiated in an inclined and spreading form. The X-ray filter 130 is provided to filter X-rays. The X-ray filter 130 needs to filter X-rays that enter at inclined angles. In order to filter the same dose of X-rays, the thickness of the attenuation and transmission portions 210 and 220 of the X-ray filter 130 through which X-rays are transmitted needs to be uniform. In other words, the X-ray filter 130 filters the radiated X-rays, and the dose of X-rays to be filtered will vary depending on the length along which the X-rays are transmitted through the X-ray filter 130. That is, a lower dose of X-rays are output through the attenuation portion 210 of the X-ray filter 130. X-rays may be further reduced when the X-rays are exposed to many surfaces of the attenuation portion 210 than when the X-rays are exposed to fewer surfaces of the attenuation portion 210. In other words, the dose of filtered X-rays may vary depending on the surfaces or path through which X-rays are transmitted through the attenuation portion 210 of the X-ray filter 130. Therefore, the X-ray filter 130 needs to have the same thickness so that X-rays can be uniformly exposed to all the portions of the X-ray filter 130. The distance from the X-ray generator 110 to the point at which an X-ray is vertically radiated onto the X-ray filter 130 is relatively short. Furthermore, the distance from the X-ray generator 110 to an end (an outermost point) of the X-ray filter 130 is relatively long because an X-ray is radiated onto the end of the X-ray filter 130 while being spread. Furthermore, X-rays are radiated in inclined directions. The thickness of the attenuation portions 210 is relatively thick in a portion onto which an X-ray is vertically radiated and gradually decreases in outward directions so that the attenuation portions 210 may be exposed to the same dose of X-rays regardless of whether X-rays are radiated vertically or in an inclined direction. This is intended to prevent an X-ray from being filtered on an outer side more than the point onto which an X-ray is vertically radiated in the case of the same thickness because the X-ray is radiated at a lower inclined angle on the outer side.

The size of the attenuation portions 210 and the transmission portions 220 is determined such that the area formed on the surface of the X-ray detector by X-rays transmitted through an attenuation portion 210 or X-rays transmitted through a transmission portion 220 is an integer multiple of the minimum measurement unit area of the X-ray detector 120.

The X-ray detector may include a plurality of charge coupled device (CCD) sensors or CCD image sensors in order to detect X-rays. In general, the minimum unit of the CCD sensors of the X-ray detector 120 may be equal to or smaller than the size of X-rays that have been transmitted through each of the attenuation and transmission portions 210 and 220 of the X-ray filter 130. The X-ray filter 130 may be disposed closer to the X-ray generator 110, and may be disposed closer to the X-ray detector 120. X-rays are generated by the X-ray generator 110, are filtered by the X-ray filter 130, and then reach the X-ray detector 120. The area of one unit of X-rays filtered by the X-ray filter 130 (X-rays filtered through one unit of the attenuation or transmission portions 210 or 220) is an integer multiple of the measurement unit area of the CCD sensors of the X-ray detector.

The medical image processing unit 140 generates medical images respectively corresponding to the two dose types recognized by the X-ray detector 120.

The medical image processing unit 140 may generate X-ray images based on a higher dose of X-rays (a higher dose of lower-energy X-rays) and a lower dose of X-rays (a lower dose of higher-energy X-rays) recognized by the X-ray detector 120. Interpolation needs to be performed in order to generate medical images in the medical image processing unit 140. Interpolation is the operation of estimating a value located between the known values of points from the known values.

The medical image processing unit 140 generates a temporary higher-dose image in which portions corresponding to a lower dose type are empty based on recognized information about portions corresponding to a higher one of the two dose types recognized by the X-ray detector 120 and estimates the empty portions based on the information of the temporary higher-dose image, thereby generating a final higher-dose image. The medical image processing unit 140 separates a higher dose of X-rays (a higher dose of lower-energy X-rays) and a lower dose of X-rays (a lower dose of higher-energy X-rays) recognized by the X-ray detector 120, and extracts images for the higher dose of X-rays and the lower dose of X-rays, respectively. The medical image processing unit 140 may fill the empty portions through an interpolation method, acquire two images from 2D projection data through a horizontal method and a vertical method in order to apply the interpolation method, and convert the two images into a single image by applying a merge method. The medical image processing unit 140 may apply this scheme to a higher-dose image and a lower-dose image. In order to minimize image distortion and reduce noise, a higher-dose image and a lower-dose image may be finally acquired by applying Gaussian filtering and median filtering.

The X-ray detector 120 simultaneously detects regions of a lower dose of X-rays (a lower dose of higher-energy X-rays) and a higher dose of X-rays (a higher dose of low-energy X-rays). When the medical image processing unit 140 extracts only the regions of the higher dose of low-energy X-rays recognized by the X-ray detector 120, the regions of the lower dose of high-energy X-rays will be empty. When generating a higher-dose image using a higher dose of X-rays (a higher dose of lower-energy X-rays), the medical image processing unit 140 extracts the higher dose of X-rays recognized by the X-ray detector 120 and estimates the shape of an empty portion corresponding to a lower dose of X-rays (a lower dose of higher-energy X-rays), thereby generating a higher-dose image. In the same manner, in order to generate a lower-dose image, the medical image processing unit 140 extracts portions corresponding to a lower dose of higher-energy X-rays recognized by the X-ray detector 120 and estimates empty portions corresponding to a higher dose of lower-energy X-rays, thereby generate a final lower-dose image.

Figure 2:
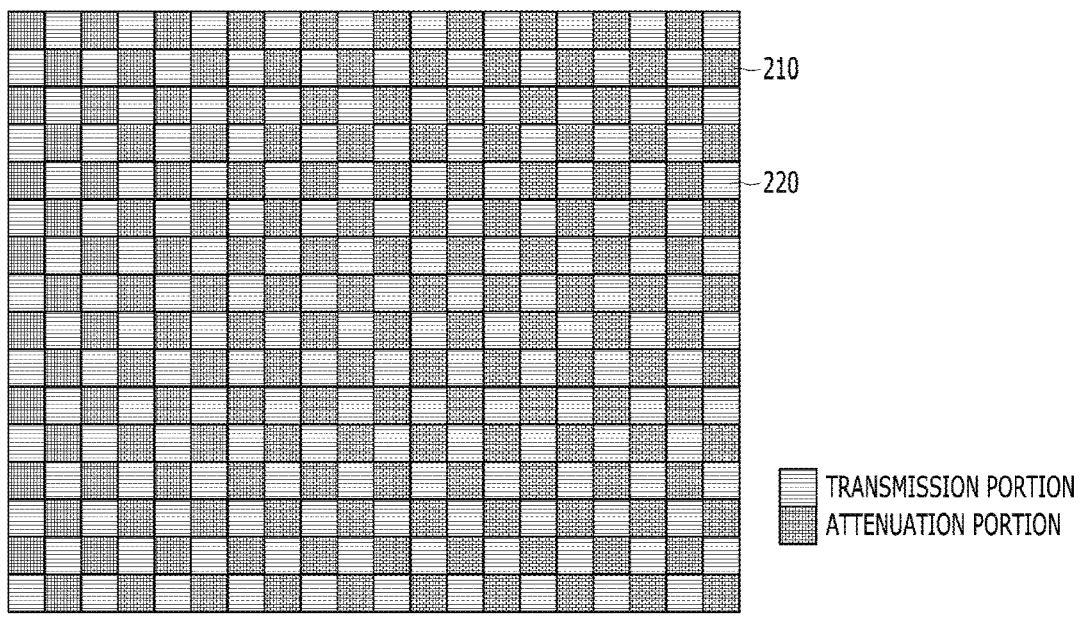
FIG. 2 is a view showing an example of the front surface of an X-ray filter having a grid pattern according to an embodiment of the present invention.

FIG. 2 is a view showing an example of the front surface of an X-ray filter having a grid pattern according to an embodiment of the present invention.

In this X-ray filter, attenuation portions and transmission portions may be arranged to form a grid pattern.

The attenuation and transmission portions of the X-ray filter may be disposed in the grid pattern. When this X-ray filter is exposed to generated X-rays, a lower dose of X-rays are output through the attenuation portions, and a higher dose of X-rays are output through the transmission portions. The filtered X-rays may be received by the X-ray detector and recognized based on the grid pattern in which the attenuation and transmission portions are arranged. In other words, the lower dose of X-rays are output through the attenuation portions, and the higher dose of X-rays are output through the transmission portions. Accordingly, the X-ray detector may detect the X-rays based on the grip pattern.

Figure 3:
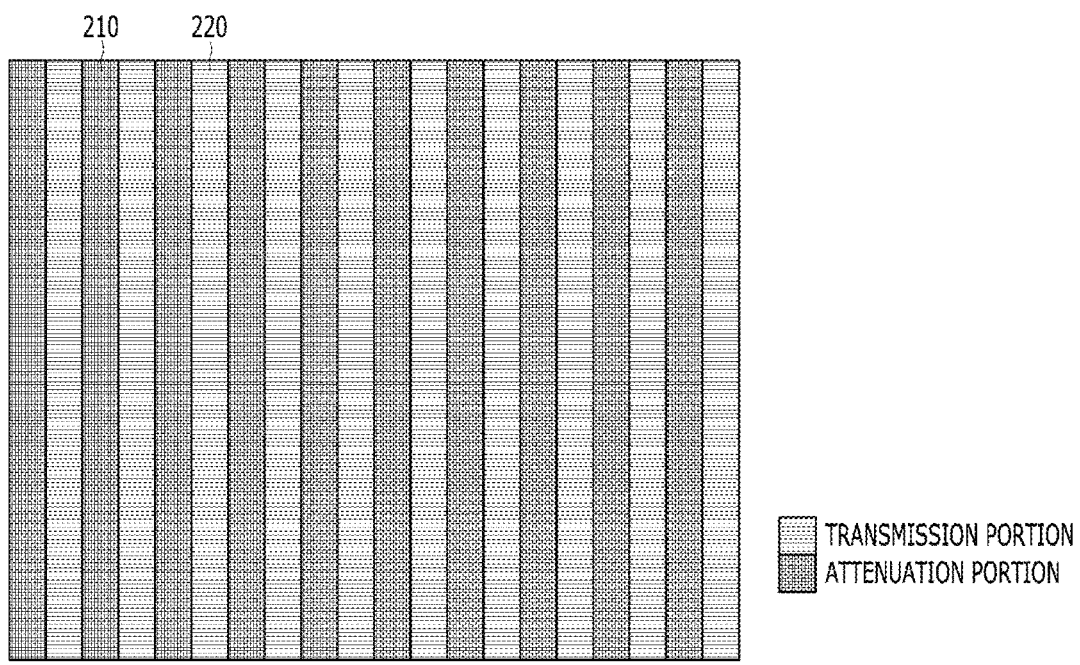
FIG. 3 is a view showing an example of the front surface of an X-ray filter having a stripe pattern according to an embodiment of the present invention.

FIG. 3 is a view showing an example of the front surface of an X-ray filter having a stripe pattern according to an embodiment of the present invention.

The attenuation portions and the transmission portions may be arranged to form a stripe pattern in which the attenuation portions and the transmission portions are alternately arranged.

The attenuation and transmission portions of the X-ray filter may be disposed in the stripe pattern. When this X-ray filter is exposed to the generated X-rays, a lower dose of X-rays are output through the attenuation portions, and a higher dose of X-rays are output through the transmission portions. The filtered X-rays may be received by the X-ray detector and recognized based on the stripe pattern of the X-rays. In other words, the lower dose of X-rays are output through the attenuation portions, and the higher dose of X-rays are output through the transmission portions. Accordingly, the X-ray detector may detect the X-rays in the order of a lower dose of X-rays, a higher dose of X-rays, a lower dose of X-rays, a higher dose of X-rays, . . . .

Figure 4:
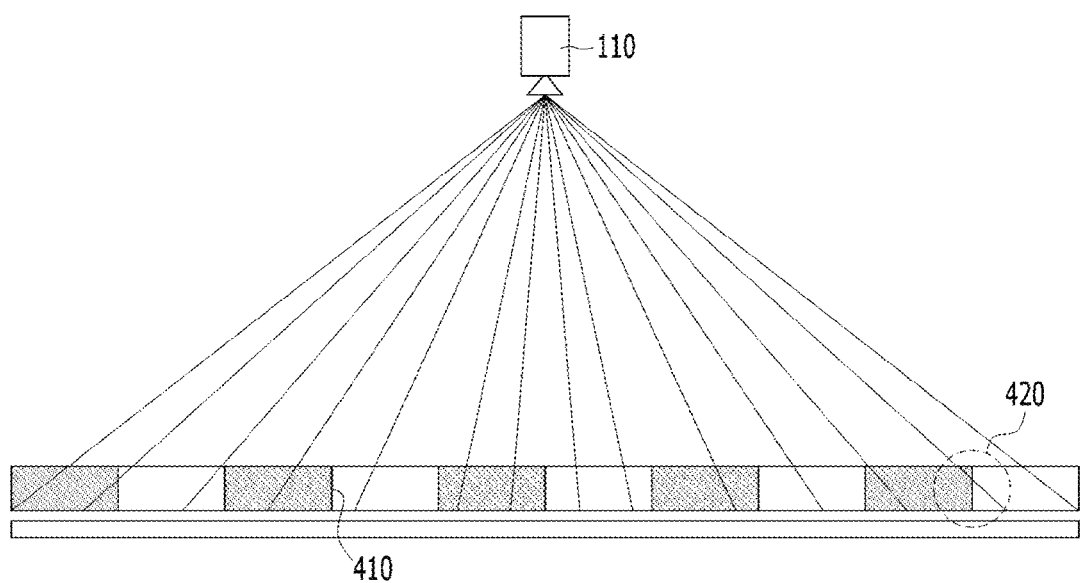
FIG. 4 is a view showing an example of the side surface of an X-ray filter in which the boundary surfaces between attenuation portions and transmission portions according to an embodiment of the present invention are vertical.

FIG. 4 is a view showing an example of the side surface of an X-ray filter in which the boundary surfaces between attenuation portions and transmission portions according to an embodiment of the present invention are vertical.

The boundary surfaces between the attenuation portions and the transmission portions are inclined toward the X-ray generator.

In the case where the boundary surfaces between the attenuation and transmission portions of the X-ray filter 130 are not inclined toward the X-ray generator but are vertical (in the case of 410), when the X-ray generator radiates X-rays toward the X-ray detector at inclined angles, there may occur a case 420 where an X-ray is transmitted through both the attenuation portion and the transmission portion. When an X-ray is radiated while being transmitted through both the attenuation portion and the transmission portion, there occurs the effect in which the X-ray is transmitted and is also attenuated, and thus a problem arises in that the X-ray may not be accurately filtered. In contrast, in the case where the boundary surfaces between the attenuation portions and the transmission portions are inclined toward the X-ray generator, a case where an X-ray is transmitted through both the attenuation portion and the transmission portion does not occur, and thus an advantage arises in that X-rays may be accurately filtered.

Figure 5:
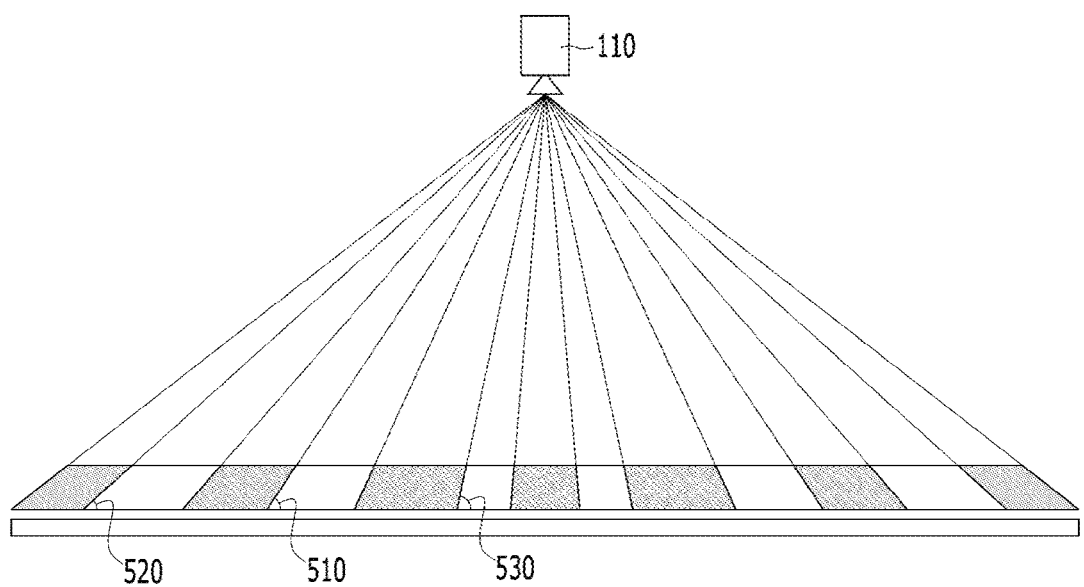
FIG. 5 is a view showing an example of the side surface of an X-ray filter in which the boundary surfaces between attenuation portions and transmission portions according to an embodiment of the present invention are inclined.

FIG. 5 is a view showing an example of the side surface of an X-ray filter in which the boundary surfaces between attenuation portions and transmission portions according to an embodiment of the present invention are inclined.

The boundary surfaces between the attenuation portions and the transmission portions are inclined toward an X-ray generator (in the case of 510).

The X-ray generator radiates X-rays toward the X-ray detector. When X-rays are radiated from the X-ray generator toward the X-ray detector, the X-rays are radiated in a form spreading from the X-ray generator to the X-ray detector. When viewed from the X-ray generator and the X-ray detector, the X-rays are radiated at inclined angles rather than straight forward. Depending on the direction in which X-rays are radiated, the directions of the attenuation portions and transmission portions of the X-ray filter are also inclined toward the X-ray generator. In the case where the boundary surfaces between the attenuation portions and the transmission portions are inclined toward the X-ray generator, when the X-ray generator radiates X-rays toward the X-ray filter, the X-rays may be more accurately transmitted through the attenuation portions and the transmission portions, and thus X-rays may be more accurately filtered.

For example, the angle 530 of the portion of the X-ray filter in a vertical direction from the X-ray generator to the X-ray detector will be large, and the angle 520 of the portion of the X-ray filter corresponding to an outside of the X-ray detector will be relatively small. Since the angles at which X-rays are radiated from the X-ray generator are various, the angles of the attenuation and transmission portions may also be inclined accordingly.

Figure 6:
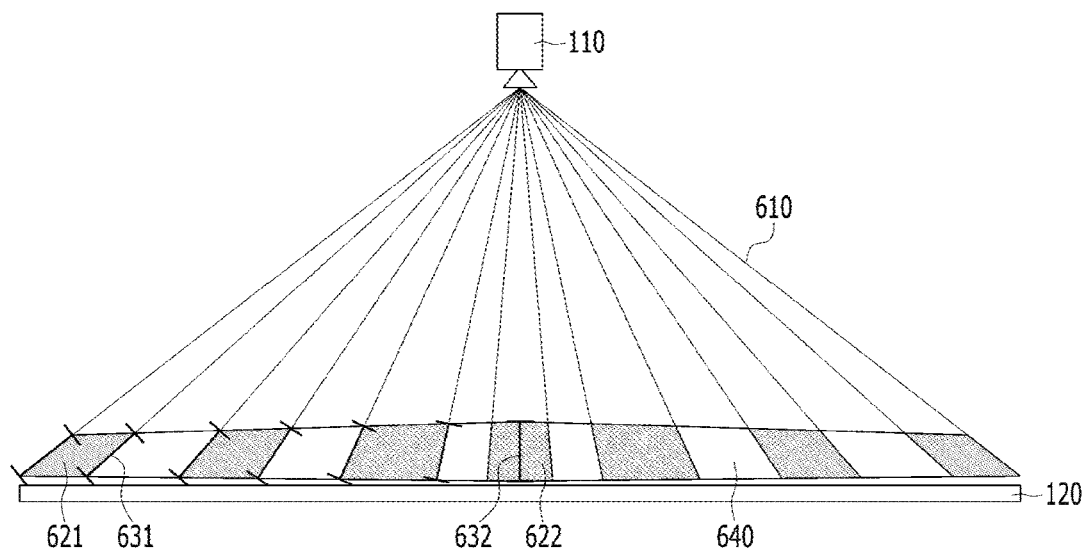
FIG. 6 is a view showing an example of the side surface of an X-ray filter in which the thickness of attenuation portions according to an embodiment of the present invention gradually decreases in outward directions.

FIG. 6 is a view showing an example of the side surface of an X-ray filter in which the thickness of attenuation portions according to an embodiment of the present invention gradually decreases in outward directions.

The thickness of the attenuation portions gradually decreases in outward directions from the point at which an X-ray is vertically radiated onto the X-ray detector.

When the X-ray generator radiates X-rays, the X-rays are radiated from the X-ray generator in the direction of the X-ray detector. In this case, the X-rays radiated by the X-ray generator are radiated in an inclined and spreading form. The X-ray filter is provided to filter X-rays. The X-ray filter needs to filter X-rays that enter at inclined angles. In order to filter the same dose of X-rays, the thickness of the attenuation and transmission portions 210 and 220 of the X-ray filter 130 through which X-rays are transmitted needs to be uniform. In other words, the X-ray filter filters the radiated X-rays, and the dose of X-rays to be filtered will vary depending on the length along which the X-rays are transmitted through the X-ray filter. That is, a lower dose of X-rays are output through the attenuation portion of the X-ray filter. X-rays may be further reduced when the X-rays are exposed to many surfaces of the attenuation portion than when the X-rays are exposed to fewer surfaces of the attenuation portion. In other words, the dose of filtered X-rays may vary depending on the surfaces or path through which X-rays are transmitted through the attenuation portion 210 of the X-ray filter. Therefore, the X-ray filter needs to have the same thickness so that X-rays can be uniformly exposed to all the portions of the X-ray filter. The distance from the X-ray generator to the point at which an X-ray is vertically radiated onto the X-ray filter is relatively short. Furthermore, the distance from the X-ray generator to an end (an outermost point) of the X-ray filter is relatively long because an X-ray is radiated onto the end of the X-ray filter while being spread. Furthermore, X-rays are radiated in inclined directions. The thickness of the attenuation portions is relatively thick in a portion onto which an X-ray is vertically radiated and gradually decreases in outward directions so that the attenuation portions can be exposed to the same dose of X-rays regardless of whether X-rays are radiated vertically or in an inclined direction. This is intended to prevent an X-ray from being filtered on an outer side more than the point onto which an X-ray is vertically radiated in the case of the same thickness because the X-ray is radiated at a smaller inclined angle on the outer side.

For example, when the X-ray generator radiates X-rays 620, the X-rays will be recognized by the X-ray detector. Prior to the detection, the X-rays are filtered by the X-ray filter in order to extract a lower dose of X-rays (a lower dose of higher-energy X-rays) and a higher dose of X-rays (a higher dose of lower-energy X-rays). To this end, attenuation portions and transmission portions are provided. In order to make the dose of the X-rays filtered out by attenuation portion A 621 and the dose of X-rays filtered out by attenuation portion B 622 the same, the thickness 631 over which X-rays are transmitted through the attenuation portion A and the thickness 632 over which X-rays are transmitted through the attenuation portion B need to be the same. In other words, the thickness of the attenuation portion through which X-rays are transmitted may be determined based on the angle at which the X-rays are radiated. The thickness of the point onto which X-rays are vertically radiated is relatively thick, and the thickness of an outer side of the attenuation portion will be relatively thin because an X-ray is radiated at a smaller inclined angle on the outer side.

Figure 7:
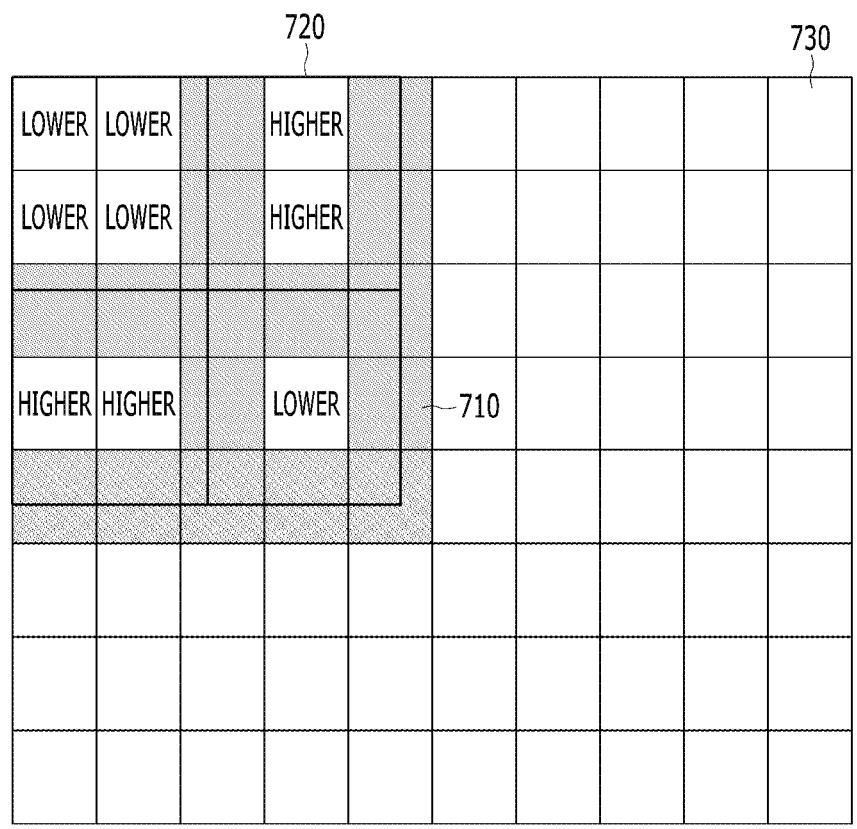
FIG. 7 is a diagram illustrating an example in which the size of attenuation and transmission portions is not an integer multiple of the unit area of a sensor for detecting X-rays according to an embodiment of the present invention.

FIG. 7 is a diagram illustrating an example in which the size of attenuation and transmission portions is not an integer multiple of the unit area of a sensor for detecting X-rays according to an embodiment of the present invention.

The size of attenuation and transmission portions, more specifically the area formed on the surface of an X-ray detector by X-rays transmitted through each attenuation portion or each transmission portion, is an integer multiple of the minimum measurement unit area of the X-ray detector.

However, when the size of the attenuation and transmission portions is not an integer multiple of the unit area of a sensor for detecting X-rays, it is difficult to accurate detect a higher dose of X-rays (a higher dose of lower-energy X-rays) and a lower dose of X-rays (a lower dose of higher-energy X-rays). For example, there is a 2×2 X-ray filter 720 having a grid pattern. The positions (1,1) and (2,2) correspond to the attenuation portions that generate a lower dose of X-rays. For ease of understanding, when the top left area is set to (1,1), (1,2) and (2,1) correspond to transmission portions that generate a higher dose of X-rays (a higher dose of low-energy X-rays). One unit of the attenuation and transmission portions of the X-ray filter occupies an area slightly larger than a 2×2 area of the sensor 830 that detects X-rays. In this case, although a lower dose of X-rays is recognized in the 2×2 unit of the sensor for detecting X-rays, a third unit is a part 710 that recognizes both a lower dose of X-rays and a higher dose of X-rays, and cannot recognize whether the dose of X-rays is a higher dose or a lower dose. When the size of the attenuation and transmission portions is not an integer multiple of the minimum measurement unit area of the X-ray detector, there occurs a case where both a higher dose of X-rays and a lower dose of X-rays are measured in one unit. In this case, it is not possible to accurately measure the dose of X-rays, so that improvement is required.

FIG. 8 is a diagram illustrating an example in which the size of attenuation and transmission portions is an integer multiple of the unit area of a sensor for detecting X-rays according to an embodiment of the present invention.

The size of attenuation and transmission portions, more specifically the area formed on the surface of an X-ray detector by X-rays transmitted through each attenuation portion or each transmission portion, is an integer multiple of the minimum measurement unit area of the X-ray detector.

The X-ray detector may include a plurality of charge coupled device (CCD) sensors or CCD image sensors in order to detect X-rays. In general, the minimum unit of the CCD sensors of the X-ray detector may be equal to or smaller than the size of X-rays that have been transmitted through each of the attenuation and transmission portions of the X-ray filter. The X-ray filter may be disposed closer to the X-ray generator, and may be disposed closer to the X-ray detector. X-rays are generated by the X-ray generator, are filtered by the X-ray filter, and then reach the X-ray detector. The area of one unit of X-rays filtered by the X-ray filter (X-rays filtered through one unit of the attenuation or transmission portions) is an integer multiple of the measurement unit area of the CCD sensors of the X-ray detector.

For example, there is a 2×2 X-ray filter 720 having a grid pattern. The positions (1,1) and (2,2) correspond to the attenuation portions that generate a lower dose of X-rays. For ease of understanding, when the top left area is set to (1,1), (1,2) and (2,1) correspond to transmission portions that generate a higher dose of X-rays (a higher dose of low-energy X-rays). Since one unit of the attenuation and transmission portions of the X-ray filter occupies a 2×2 area of the sensor that detects X-rays, it may be possible to accurately measure a lower dose of X-rays or a higher dose of X-rays in four units of the X-ray detector for each unit of the attenuation portions. In other words, the X-rays transmitted through the attenuation portion located at position (1,1) of the X-ray filter are recognized at positions (1,1), (1,2), (2,1) and (2,1) of the X-ray detector as a lower dose of X-rays, and the X rays transmitted through the transmission portion located at position (1,2) are recognized at positions (1,3), (1,4), (2,3) and (2,4) as a higher dose of X-rays (a higher dose of lower-energy X-rays). In the same manner, the X-rays transmitted through the attenuation portion located at position (2,1) of the X-ray filter are recognized at positions (3,1), (3,2), (4,1) and (4,1) of the X-ray detector as a higher dose of X-rays (a higher dose of lower-energy X-rays), and the X rays transmitted through the transmission portion located at position (2,2) are recognized at positions (3,3), (3,4), (4,3) and (4,4) as a lower dose of X-rays (a lower dose of higher-energy X-rays).

Figure 9:
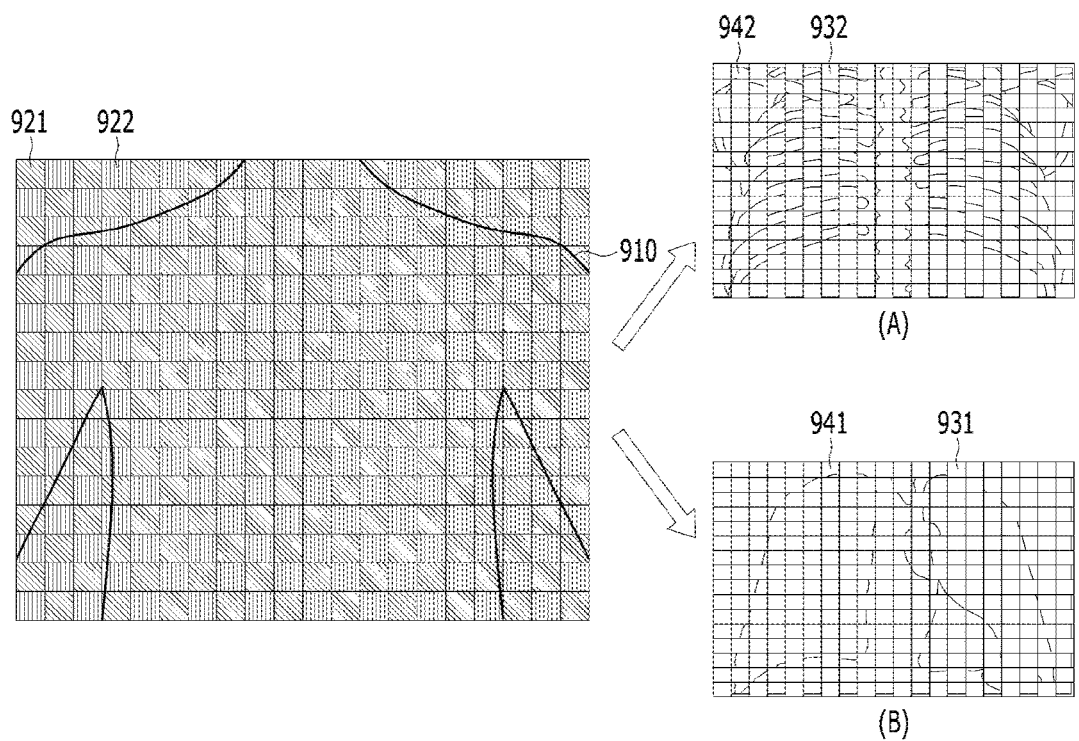
FIG. 9 is a diagram illustrating an example in which the attenuation and transmission portions of an X-ray filter according to an embodiment of the present invention recognize an object.

FIG. 9 is a diagram illustrating an example in which the attenuation and transmission portions of an X-ray filter according to an embodiment of the present invention recognize an object.

The medical image processing unit generates medical images corresponding to two dose types recognized by the X-ray detector.

The X-rays generated by the X-ray generator include both lower- and higher-energy X-rays. When the X-ray generator generates X-rays, the X-rays are transmitted through the X-ray filter, and reach the X-ray detector. The X-rays are filtered through the transmission and attenuation portions of the X-ray filter. Through the attenuation portions, lower-energy X-rays are filtered out, and higher-energy X-rays are transmitted through the X-ray filter and reach the X-ray detector. Through the transmission portions, both higher-energy X-rays and lower-energy X-rays may be transmitted therethrough and reach the X-ray detector. Accordingly, the regions through which lower-energy X-rays and higher-energy X-rays are transmitted may vary depending on the pattern of the X-ray filter.

For example, in the case where the X-ray filter has a grid pattern, when an object 910 that is the chest of a person to be X-rayed is imaged, the X-ray detector may simultaneously recognize and photograph regions of a lower dose of high-energy X-rays 921 and a higher dose of low-energy X-rays 911. Thereafter, the photographed images may be separately extracted as a higher-dose image A in which both lower-energy X-rays and higher-energy X-rays are recognized and a lower-dose image B in which higher-energy X-rays are recognized. In the higher-dose image A, portions 932 corresponding to the lower dose type are empty, and only portions 942 corresponding to the higher dose type are extracted. In the same manner, in the lower-dose image B, portions 931 corresponding to the higher dose type are empty, and only portions 941 corresponding to the lower dose type are extracted.

Figure 10:
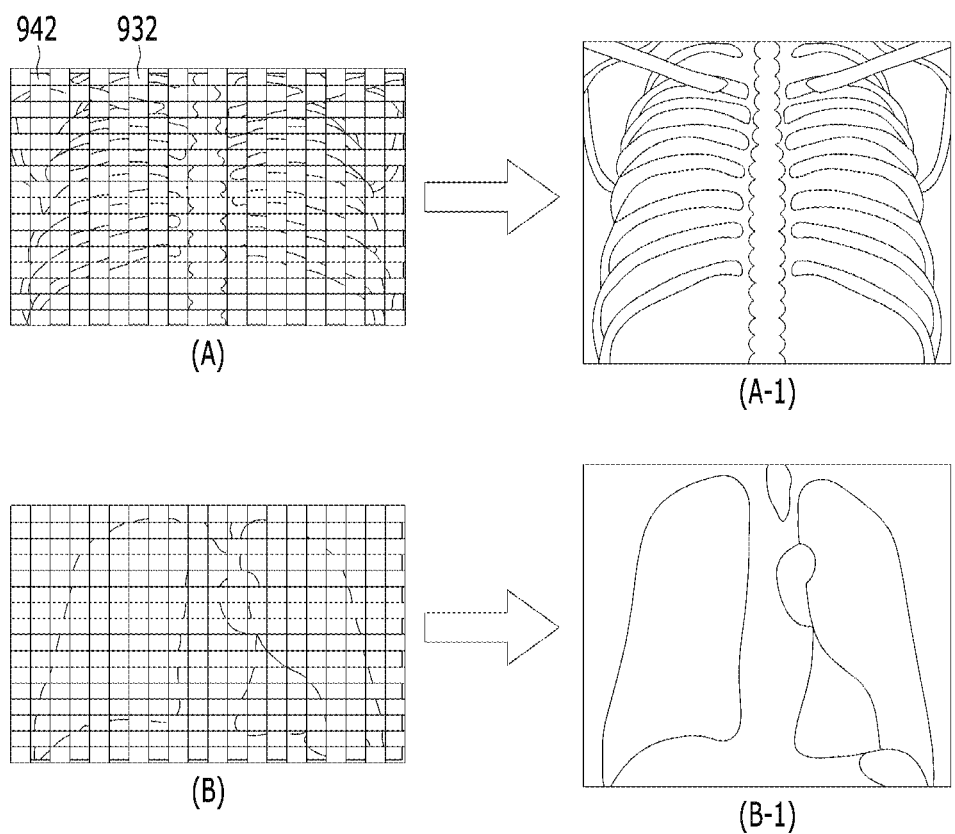
FIG. 10 is a diagram illustrating an example of extracting X-ray images based on the attenuation and transmission portions of an X-ray filter according to an embodiment of the present invention.

FIG. 10 is a diagram illustrating an example of extracting X-ray images based on the attenuation and transmission portions of an X-ray filter according to an embodiment of the present invention.

The medical image processing unit generates a temporary higher-dose image in which portions corresponding to a lower dose type are empty based on recognized information about portions corresponding to a higher one of the two dose types recognized by the X-ray detector and estimates the empty portions based on the information of the temporary higher-dose image, thereby generating a final higher-dose image.

For example, the chest of a person, which is an object, is X-rayed, and the medical image processing unit extracts a higher-dose image A and a lower-dose image B and separates them into two types of images. Based on the object, relatively hard bones are photographed by higher-dose X-rays, and organs are photographed by lower-dose X-rays. Thereafter, the medical image processing unit may estimate the empty portions of the higher-dose image A based on the higher-dose image A by using an interpolation method, and may generate a final higher-dose image A-1 in which the bones of the object are photographed. In the same manner, the medical image processing unit may estimate the empty portions of the lower-dose image B based on the lower-dose image B by using an interpolation method, and may generate a final lower-dose image B-1 in which the organs of the object are photographed.

Figure 11:
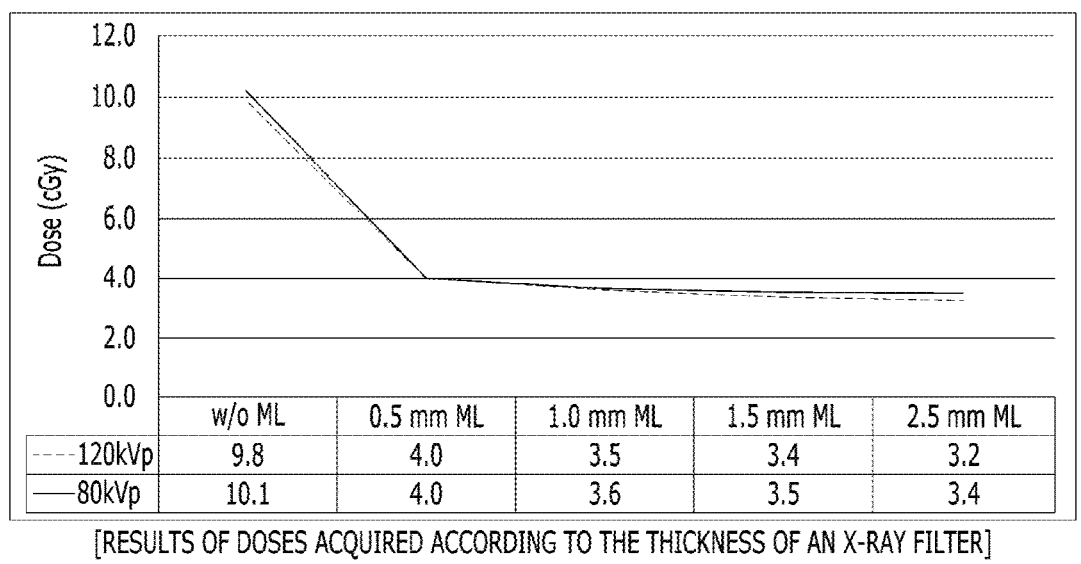
FIG. 11 is a graph showing an example of the results of doses obtained according to the thickness of an X-ray filter according to an embodiment of the present invention.

FIG. 11 is a graph showing an example of the results of doses obtained according to the thickness of an X-ray filter according to an embodiment of the present invention.

The doses for respective grid thicknesses were obtained using a uniform phantom method. The doses for respective grid thicknesses of X-ray filters were obtained by multiplying a dose conversion factor of $7.2 \times 10 \propto cGy/output$ obtained through a Gafchromic EBT3 film with result values obtained by MCNP. The results are shown in the graph of FIG. 11. As a result of calculating doses, received by the phantom when the tube voltages were 80 kVp and 120 kVp, using MCNPX, the doses at 80 kVp and 120 kVp were 10.1 cGy and 9.8 cGy, respectively. In the case of 80 kVp, the calculated dose was about 3% higher. As a result of calculating doses based on the thicknesses of the X-ray filter, when the 0.5 mm-thick X-ray filter was placed, the doses were 4.0 cGy for both tube voltages and reduced by about 40% compared to a case without the X-ray filter. When the thickness of the X-ray filter was increased up to 2.0 mm, the dose received by the phantom was decreased by about 33%. The dose attributable to the scattered rays generated by a Compton scattering reaction in the X-ray filter was 0.04% of the total dose, which was significantly low. It is determined that the reason that the dose calculated through computer simulation at a tube voltage of 80 kVp is 3% higher than the dose calculated through computer simulation at a tube voltage of 120 kVp is that more X-rays were absorbed at 80 kVp at which many relatively low-energy X-rays were present because the dose was viewed in a cell 2.0 mm inside the phantom surface in order to check for the surface dose.

FIG. 12 is a diagram illustrating the ratio of an output photon quantity to an incident photon quantity per the material and thickness of an X-ray filter according to an embodiment of the present invention.

Various types of constituent materials used for the optimization of the X-ray filter material include copper (8.96 g/cm$^3$) mainly applied to a filter for X-ray imaging, niobium (8.57 g/cm$^3$) applied to a filter for the acquisition of an dental X-ray image, stannum (7.31 g/cm$^3$) applied to a filter for dual energy CT equipment, and gold (19.32 g/cm$^3$). In addition, for thickness optimization, spectra were detected by applying X-ray filters of 0.1 mm, 0.5 mm, and 1.0 mm thickness for each material. The photon energies detected after being transmitted through X-ray filters were analyzed using a Matlab program. In order to relatively represent the magnitudes of the photon spectra transmitted through an energy modulation filter, normalization was performed based on the maximum value of a photon spectrum that was not transmitted through the X-ray filter. As a result of quantitatively comparing the average energy of the photon spectrum not transmitted through the X-ray filter and the photon spectrum transmitted through the X-ray filter in order to check for the enhancement of the ray flux caused by the X-ray filter, gold exhibited the highest average energy at a thickness of 0.1 mm. However, the average energy increase rate according to the thickness was relatively low, and the total output photon quantity was small because the quantity of photons absorbed by the filter was large. Furthermore, in the case of the photon spectrum detected by the detector after being transmitted through the X-ray filter, there may be achieved the effect in which the average photon kinetic energy is increased. However, the quantity of collected photons in the detector decreases compared to that in the case where the filter is not used. Accordingly, when a high-energy photon spectrum is used through an X-ray filter, tube current needs to be effectively corrected to maintain the image quality.

FIG. 13 is a diagram illustrating an example of the calculation of the trigonometric ratio for determining the size of the attenuating and transmission portions of the X-ray filter and parameters for determining the sizes of the attenuating and transmission portions of the X-ray filter according to an embodiment of the present invention.

In a given FOD, ODD and FDD, in order to determine the sizes of the attenuation and transmission portions when there was the X-ray filter in front of the X-ray generator and when there was the X-ray filter in front of the X-ray detector, calculation was performed using the trigonometric ratio, as shown in FIGS. 13-A, and 13-B shows the main modeling parameters obtained by the trigonometric ratio calculation. The cell size of the X-ray filter was determined through the trigonometric ratio calculation method of FIG. 13 and modeled by placing the X-ray filter in front of the X-ray generator, and then simulation was performed. The X-ray filter may have an area of 100 mm×100 mm and be composed of cells of attenuation and transmission portions having a size of about 1.066 mm.

The present invention is directed to the dual energy X-ray imaging apparatus that is capable of generating a higher-dose, lower-energy image and a lower-dose, higher-energy image by radiating X-rays once and partially attenuating the X-rays using an X-ray filter. More specifically, the present invention is directed to the dual energy X-ray imaging apparatus including: the X-ray generator configured to generate a predetermined dose of X-rays; the X-ray detector configured to detect the X-rays received from the X-ray generator; the X-ray filter located between the X-ray generator and the X-ray detector, and configured to filter out part of the generated X-rays so that X-rays of two dose types reach the X-ray detector; and the medical image processing unit configured to generate medical images corresponding to the two dose types recognized by the X-ray detector.

The present invention provides the dual-energy X-ray imaging apparatus that may expose the human body to less radiation and also acquire X-ray images of two different dose types by radiating X-rays only once.

The present invention provides the dual-energy X-ray imaging apparatus that may acquire two types of X-rays, i.e., a lower dose of high-energy X-rays and a higher dose of low-energy X-rays, using the single filter by attenuating or not attenuating a predetermined dose of generated X-rays.

The present invention provides the dual-energy X-ray imaging apparatus that may easily estimate X-ray images using X-rays filtered through the attenuation and transmission portions by applying the filter having a specific grid pattern and thus arranging the attenuation and transmission portions regularly.

The present invention provides the dual-energy X-ray imaging apparatus that may allow the boundary surfaces between the attenuation and transmission portions to be inclined toward the X-ray generator, so that X-rays are not transmitted through both attenuation and transmission portions but are transmitted through only one of the attenuation and transmission portions, thereby enabling generated X-rays to be more accurately recognized.

The present invention provides the dual-energy X-ray imaging apparatus that may allow the thickness of the attenuation portions to gradually decrease in outward directions from the point onto which an X-ray is vertically radiated by the X-ray detector, so that the dose of attenuated X-rays for X-rays radiated vertically and the dose of attenuated X-rays for X-rays radiated at an inclined angle may be made the same.

The present invention provides the dual-energy X-ray imaging apparatus that may allow the size of the attenuation and transmission portions to be an integer multiple of the minimum measurement unit area of the X-ray detector, so that the minimum measurement unit of the X-ray detector recognizes only an X-ray transmitted through one of the attenuation and transmission portions, thereby clearly distinguishing between a lower dose of X-rays and a higher dose of X-rays.

The present invention provides the dual-energy X-ray imaging apparatus that may generate a higher-dose image by estimating empty portions corresponding to a lower dose of X-rays based on recognized information about portions corresponding to a higher dose of X-rays, so that two types of X-ray images may be generated by filtering out part of X-rays, radiated once, using the single X-ray filter.

Although the specific embodiments of the present invention have been disclosed for illustrative purposes, those skilled in the art will appreciate that various modifications, additions and substitutions are possible without departing from the scope and spirit of the invention as disclosed in the accompanying claims.

What is claimed is:

1. A dual energy X-ray imaging apparatus comprising:
an X-ray generator configured to generate a predetermined dose of X-rays;
an X-ray detector configured to detect the X-rays received from the X-ray generator;
an X-ray filter located between the X-ray generator and the X-ray detector, and configured to filter out part of the generated X-rays so that X-rays of two dose types reach the X-ray detector; and
a medical image processing unit configured to generate medical images respectively corresponding to the two dose types recognized by the X-ray detector,
wherein the X-ray filter comprises:
attenuation portions made of at least one of lead, copper, niobium, stannum, or gold, and configured to attenuate the predetermined dose of the generated X-rays; and
transmission portions configured to transmit a higher dose of X-rays than the attenuation portions therethrough,
wherein the attenuation portions and the transmission portions are arranged to form a grid pattern, and
wherein boundary surfaces between the attenuation portions and the transmission portions are inclined toward the X-ray generator.

2. The dual energy X-ray imaging apparatus of claim 1, wherein a thickness of the attenuation portions gradually decreases in outward directions from a point at which an X-ray is vertically radiated onto the X-ray detector.

3. The dual energy X-ray imaging apparatus of claim 1, wherein a size of the attenuation and transmission portions is determined such that an area formed on a surface of the X-ray detector by X-rays transmitted through one of the attenuation portions or X-rays transmitted through one of the transmission portions is an integer multiple of a minimum measurement unit area of the X-ray detector.

4. The dual energy X-ray imaging apparatus of claim 1, wherein the medical image processing unit is further configured to:
generate a temporary higher-dose image in which portions corresponding to a lower dose type are empty based on recognized information about portions corresponding to a higher one of the two dose types recognized by the X-ray detector; and
estimate the empty portions based on information of the temporary higher-dose image, thereby generating a final higher-dose image.

* * * * *